United States Patent [19]

Aitcheson et al.

[11] Patent Number: 4,994,213
[45] Date of Patent: Feb. 19, 1991

[54] METHOD OF PREPARING LIPID STRUCTURES

[75] Inventors: David F. Aitcheson, San Jose; Renee A. Tenzel, Mountain View, both of Calif.

[73] Assignee: Liposome Technology, Inc., Menlo Park, Calif.

[21] Appl. No.: 194,838

[22] Filed: May 17, 1988

[51] Int. Cl.$^5$ .................. A61K 9/133; A61K 9/127; B01J 13/12

[52] U.S. Cl. .................. 264/4.6; 264/4.1; 424/450

[58] Field of Search .................. 264/4.1, 4.3, 4.6, 4.7; 428/402.2; 424/450

[56] References Cited

U.S. PATENT DOCUMENTS

| | | | |
|---|---|---|---|
| 4,235,871 | 11/1980 | Papahadjopoulos et al. | 264/4.6 |
| 4,438,052 | 5/1984 | Weder et al. | 264/4.6 |
| 4,588,578 | 5/1986 | Fountain et al. | 428/402.2 X |
| 4,622,188 | 11/1986 | Adamich et al. | 264/4.6 |
| 4,731,210 | 3/1988 | Weder et al. | 264/4.3 |
| 4,752,425 | 6/1988 | Martin et al. | 264/4.6 |

FOREIGN PATENT DOCUMENTS 0055576 7/1982 European Pat. Off. .

OTHER PUBLICATIONS

Batzri et al.: "Single Bilayer Liposomes ...", *Biochim. Biophys. Acta.*, vol. 298, pp. 1015-1019, 1973.
Kremer et al.: "Vesicles of Variable Diameter ...", *Biochemistry*, vol. 16, No. 17, 1977, pp. 3932-3935.

*Primary Examiner*—Richard D. Lovering
*Assistant Examiner*—John M. Covert
*Attorney, Agent, or Firm*—Peter J. Dehlinger

[57] ABSTRACT

A method of forming lipid structures, such as liposomes is disclosed. Lipids are dissolved in a solvent system containing a water-miscible solvent, such as ethanol, and an aqueous medium. The water:solvent ratio is raised by removing water and solvent in a reverse osmosis system, and replacing lost solvent with added aqueous medium, preferably at a rate which just balances volume loss by reverse osmosis. In one embodiment, the method is used to produce uniform-size liposomes.

11 Claims, 4 Drawing Sheets

METHOD OF PREPARING LIPID STRUCTURES

1. FIELD OF THE INVENTION

The present invention relates to a method of preparing lipid structures such as liposomes.

2. REFERENCES

Gregoriadis, G., in *Liposomes*, Vol. III.
Poznansky, M. L., et al, Pharm Revs, 36(4):277 (1984).
Szoka, F., et al, Proc Nat Acad Sci (USA) 75:4194 (1978).
Szoka, F., et al, Ann Rev Biophys Bioeng, 9:467 (1980).

3. BACKGROUND OF THE INVENTION

The use of liposomes and other lipid structures, such as micro-emulsions, micelles, and drug/lipid complexes, for drug delivery has been widely proposed. Such lipid structures, and particularly liposomes, have the potential for providing controlled "depot" release of an administered drug over an extended time period, and of reducing the side effects of the drug, by limiting the concentration of free drug in the bloodstream. These advantages apply to a variety of routes of administration, including intravenous, intramuscular, and subcutaneous, application to mucosal tissue, or delivery by inhalation. Where liposomes are administered by intravenous delivery, liposomes provide a further advantage of altering the tissue distribution of the drug. Liposome drug delivery systems have been reviewed (Poznansky, Gregoriadis).

In the case of liposomes, optimal size for use in parenteral administration is generally between about 100 nm and 300 nm. Liposomes in this size range can be sterilized by passage through conventional filters having a particle size discrimination of about 200 nm. This size range of liposomes also favors biodistribution in certain target organs, such as liver, spleen, and bone marrow (Gabizon), and gives more uniform and predictable drug-release rates and stability in the bloodstream. Liposomes whose sizes are less than about 300 nm also show less tendency to agglutinate on storage, and are thus generally safer and less toxic in parenteral use than larger-size liposomes.

It may also be desirable to prepare uniformsize liposomes in a selected size range less than about 100 nm. For example, small unilamellar vesicles (SUVs) having sizes between about 30–80 nm are useful in targeting to tumor tissue or to hepatocyte cells, because of their ability to penetrate the endothelial lining of capillaries. SUVs are also advantageous in ophthalmic liposome formulations, because of the greater optical clarity of the smaller liposomes.

Many techniques for preparing liposomes and other lipid structures have been proposed (e.g., Szoka 1983). Typically, prior art liposome preparation methods yield liposomes which are heterodisperse, and predominantly greater than about 1 micron (1,000 nm) in size. These initial heterodisperse suspensions can be reduced in size and size distribution by a number of known methods. One size-processing method which is suitable for large-scale production is homogenization. Here an initial heterodisperse liposome preparation is pumped under high pressure through a small orifice or reaction chamber. The suspension is usually cycled through the reaction chamber until a desired average size of liposome particles is achieved. A limitation of this method is that the liposome size distribution is typically quite broad and variable, depending on a number of process variables, such as pressure, number of homogenization cycles, and internal temperature. Also, the processed fluid tends to pick up metal and oil contaminants from the homogenizer pump, and may be further contaminated by residual chemical agents used to sterilize the pump seals.

Sonication, or ultrasonic irradiation, is another method that is used for reducing liposome sizes by shearing, and especially for preparing SUVs. The processing capacity of this method is quite limited, since long-term sonication of relatively small volumes is required. Also, localized heat build-up during sonication can lead to peroxidative damage to the lipids, and sonic probes shed titanium particles which are potentially quite toxic in vivo.

A third general size-processing method known in the prior art is based on liposome extrusion through uniform pore-size polycarbonate membranes (Szoka 1978). This procedure has advantages over homogenization and sonication methods in that several membrane pore sizes are available for producing liposomes in different selected size ranges. In addition, the size distribution of the liposomes can be made quite narrow, particularly by cycling the material through the selected-size filter several times. Nonetheless, the membrane extrusion method has limitations in large-scale processing, including problems of membrane clogging, membrane fragility, and relatively slow throughput Co-owned U.S. Pat. No. 4,737,323 for "Liposome Extrusion Method" describes a liposome sizing method in which heterogeneous-size liposomes are sized by extrusion through an asymmetric ceramic filter. This method allows greater throughput rates, and avoids problems of clogging since high extrusion pressure and reverse-direction flow can be employed. However, like the membrane extrusion method, the filter-extrusion method requires post-liposome formation sizing. Further, the method may be limited where uniform-size SUVs are desired.

One limitation of all of the above-mentioned methods is the loss of encapsulated material as large liposomes are broken and reformed as smaller vesicles.

In none of the liposome-preparation methods mentioned above are liposomes with a narrow, substantially symmetrical size distribution produced.

4. SUMMARY OF THE INVENTION

It is a general object to provide a novel method of preparing a variety of lipid structures, including liposomes, micelles, and emulsion particles.

It is a more specific object of the invention to provide a liposome preparation method which solves or substantially overcomes above-mentioned problems associated with the prior art.

Another object is to provide such a method which can be used to produce uniform-size liposomes, without any requirement for a shearing and/or extrusion processing steps after initial liposome formation.

Still another object of the invention is to provide such a method which can be practiced to achieve uniform liposome sizes, and relatively high encapsulation rates, and in which loss of non-encapsulated material is minimized.

It is another object of the invention to provide a novel method for preparing uniform-size small unilamellar vesicles (SUVs) without requiring sonication or other post-liposome formation shearing procedures.

In practicing the method of the invention, there is first formed a mixture of lipids in a single phase solvent system containing a water-miscible lipid solvent and water. The water:solvent ratio of the mixture is raised by removing solvent and water from the mixture by reverse osmosis, and, as the solvent and water are removed, by adding aqueous medium to the mixture, until lipid-structure formation occurs.

In a preferred embodiment of the invention, the addition of aqueous medium to the mixture is controlled to balance the removal of solvent and water by reverse osmosis, to maintain the volume of the mixture substantially constant during lipid structure formation. In the case of liposome formation, the resulting liposomes have a narrow, substantially symmetrical size distribution.

According to another aspect of the invention, the average size of the liposomes formed can be varied selectively, from about 30-300 nm, according to lipid composition and ionic strength of the mixture. By way of example, SUVs are formed with neutral lipid components, and with lipid components containing 5-10 mole percent negatively charged phospholipid at low ionic strength during liposome formation. Liposomes with average sizes about 250 nm are formed with lipid components containing 5-10 mole percent negatively charged phospholipid at higher ionic strength.

The invention also includes a unique method for producing SUVs without post-liposome formation shear processing.

These and other objects and features of the invention will become more fully appreciated when the following detailed description of the invention is read in conjunction with the accompanying drawings.

DETAILED DESCRIPTION OF THE INVENTION

A. Lipid/Solvent/Water Mixture

The lipid/solvent/water mixture formed in practicing the invention is composed of lipids, a water-miscible lipid solvent, and an aqueous medium, which preferably includes charged solute components.

Where the method is used in forming liposomes, the lipids are vesicle-forming lipids which generally include neutral and negatively charged phospholipids, such as phosphatidylcholine (PC) and phosphatidylglycerol (PG). The vesicle-forming lipids may also include sterol lipids, such as cholesterol, and/or glycolipids, such phosphatidylinositol, gangliosides, and the like. A variety of lipids having selected acyl chain compositions are commercially available or may be obtained by standard lipid isolation procedures.

One factor in the choice of lipid components in the mixture is the size-effect of charged lipid species. For example, egg PC (with no charged lipid) produces uniform-size liposomes having average sizes of about 30-60 nm. By contrast, a lipid composition containing 95% egg PC and 5% egg PG yields an average liposome size which is dependent on ionic strength (Example 1 and 2).

Where the method is used to produce other lipid structures, suitable lipid components, such as triglycerides for producing emulsions, and a variety of amphipathic lipids, such as fatty acids, for producing micelles, are employed.

The water-miscible lipid solvent in the mixture is defined herein as one which can be mixed with an aqueous medium in substantially any proportion without forming a two-phase system. Preferred solvents are small alcohols, such as ethanol, methanol, propanol, and isopropanol, dimethylsulfoxide (DMSO). The solvent may contain additional solvent components, such as chloroform, acetone, or chlorofluorocarbon solvents, which are typically added to increase lipid solubility, and are present at a sufficiently low concentrations that solvent phase separation does not occur. For example, one suitable solvent for preparing liposomes containing phospholipid and cholesterol components contains ethanol as primary solvent component and between about 10%–20% chlorofluorocarbon solvent.

As indicated above, the ionic strength of the mixture during liposome formation may determine liposome mean diameter, when charged lipid components are present. As seen in Examples 1 and 2, a relatively low ionic strength results in liposome sizes less than about 50 nm, whereas at a tenfold higher ionic strength, liposome sizes in the 200-300 nm range are produced. The ionic component of the mixture is typically provided by a salt, such as sodium or potassium chloride or phosphate salts, which is preferably added as an aqueous salt or buffer solution to the lipid solvent. Alternatively, the ionic component may include a charged compound which is to be encapsulated or entrapped in liposomes. For forming SUVs with an average size of less than about 50 nm, and with charged lipid components, the ionic strength of the medium during liposome formation is typically less than about 30 mM, and preferably between about 5-20 mM. Alternatively, where neutral lipid components alone are used, the size of the liposomes is relatively independent of ionic strength.

In preparing the lipid/solvent/water mixture, the selected lipids are preferably first dissolved in the lipid solvent. The amount of lipid added is calculated to give a final lipid concentration in the mixture of less than about 250-300 umole/ml, depending on desired final lipid concentration and encapsulation efficiency. The lipid solution may also include lipophilic drug components which are to be entrapped in the lipid structures.

The aqueous medium used in forming the final lipid/solvent/water mixture may include salts or other ionic species and water-soluble drug compounds which are to be encapsulated in the liposomes. Typically, a relatively small portion of the aqueous medium is added to the solvent mixture by dilution, prior to reverse osmosis (RO). The solvent is then substantially exchanged with aqueous medium by reverse osmosis, as described below in Section B. The procedure described in Examples 1 and 2 is illustrative. Here an initial lipid in ethanol solution is diluted with distilled water to a final water:solvent volume ratio of about 1:9. Additional aqueous medium is then added as solvent and water are removed by RO, at a rate which maintains the volume of the mixture substantially constant, by addition of aqueous medium containing the desired salt concentration.

As the water:solvent volume ratio of the mixture is increased, during reverse osmosis, a mixture containing vesicle-forming lipids typically become translucent. With continued replacement of solvent by aqueous medium, lipid aggregates or assemblies which appear to include large vesicular structures as well as amorphous lipid bodies (as observed by light microscopy) begin to form. In the case of ethanol as solvent, the solvent ratio at which lipid structure first form is typically between about 40%-55%, depending on lipid concentration and percent charged lipid components. Experiments conducted in support of the present invention show that the lipid structure assembly occurs at about 56% ethanol for uncharged lipid components, and falls to about 40% ethanol as the percent negatively charged lipid is increased to about 30 mole percent.

B. Solvent Exchange by Reverse Osmosis

Figure 1:
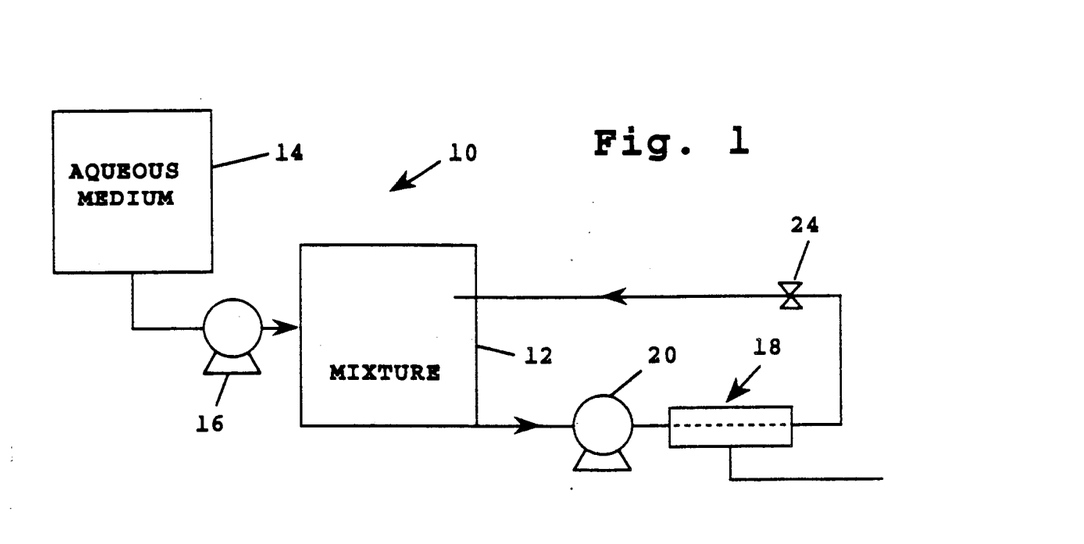
FIG. 1 is a schematic drawing of a reverse osmosis system used in practicing the present invention.

FIG. 1 shows a reverse osmosis (RO) system 10 designed for solvent exchange in a lipid-structure preparation method. The system includes a holding tank 12, and a vessel 14 which feeds the aqueous medium to the tank, at a controlled rate, via a pump 16. In a specific embodiment of the invention, where the volume of the mixture in the tank is maintained at about 1 liter, the pump is operated to supply medium to the tank at between about 5-200 ml/min and preferably about 8-50 ml/min, and the pumping rate is preferably controlled to match the rate of removal of liquid from the tank by RO filtration.

A crossflow RO filter 18 is connected to the tank through a high pressure pump 20 which circulates the fluid in the tank in the direction shown. The speed of the pump is adjustable to regulate the rate of fluid flow through the filter. The pump speed is typically set to a flow rate of about 80% of the maximum. A valve 24 is adjustable to control the pressure within the filtration device. Typically the filtration pressure is between about 400-600 psi.

Filter 18 is selected on the basis of ability to pass the solvent(s) in the lipid/solvent/water mixture. RO filters designed for passage of a variety of small, water-miscible solvents are commercially available, such as from Millipore Corporation (Bedford, Mass.).

In operation, a given volume of lipid/solvent or lipid/solvent/water mixture is added to the tank. In a preferred embodiment, the water:solvent ratio in the initial mixture is substantially less than that at which lipid assembly first occurs. A first aqueous medium stored in vessel 14 preferably contains the solute molecules to be encapsulated or entrapped in the lipid structures, and salt or other ionic species added to control particle size, in the case of liposomes. If the compound to be encapsulated is contained in the first wash, the total volume of the wash preferably should be no greater than that required to bring the mixture in the tank to the lipid assembly point. In the method illustrated in Examples 1 and 2, where the first aqueous-medium volume contains the ionic species in the mixture, but not drug solute molecules, the aqueousmedium volume and the initial mixture in the tank both have the same 1 liter volume. Four additional volumes of distilled water are added to remove all but residual amounts of the solvent from the liposome preparation.

Figure 2:
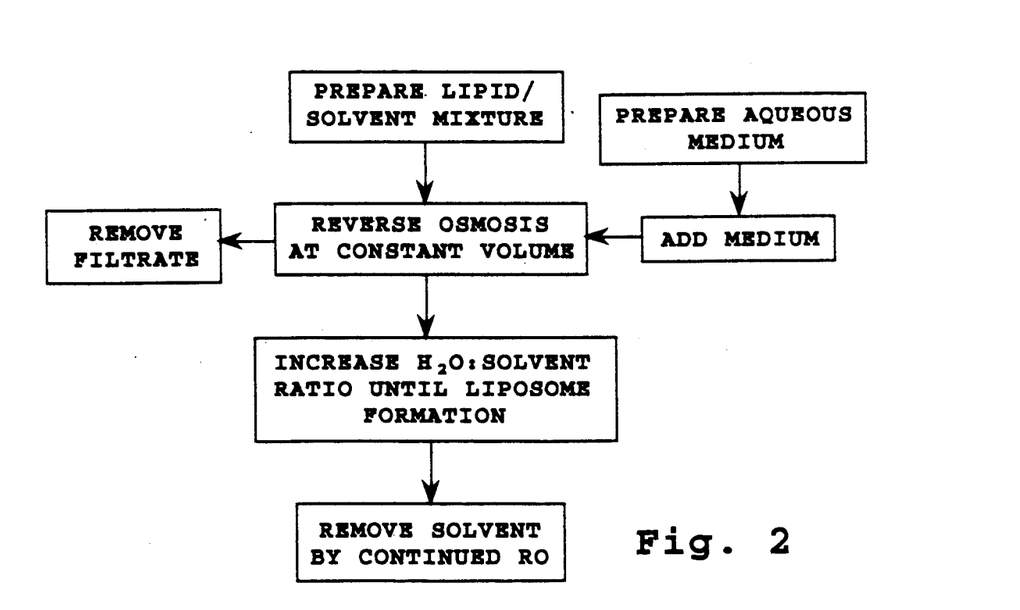
FIG. 2 is a flow diagram of the steps used in practicing the invention.

FIG. 2 is a flow diagram of the processing steps in the RO method, as exemplified for liposome formation. The reverse osmosis step in the diagram involves circulating the tank mixture under pressure across an RO membrane, with addition of aqueous medium from vessel 14 to balance solvent/water RO filtrate loss. As the water:solvent ratio in the system is raised, the mixture will reach a water:solvent ratio at which lipid assembly first occurs. With continued solvent exchange, the mixture passes through the stage where large lipid aggregates reform, with the final reformation producing uniform-size liposomes having the selected average size. After final liposome formation, the solvent is conveniently removed by continued RO, with addition of several volumes of distilled water.

Figure 3:
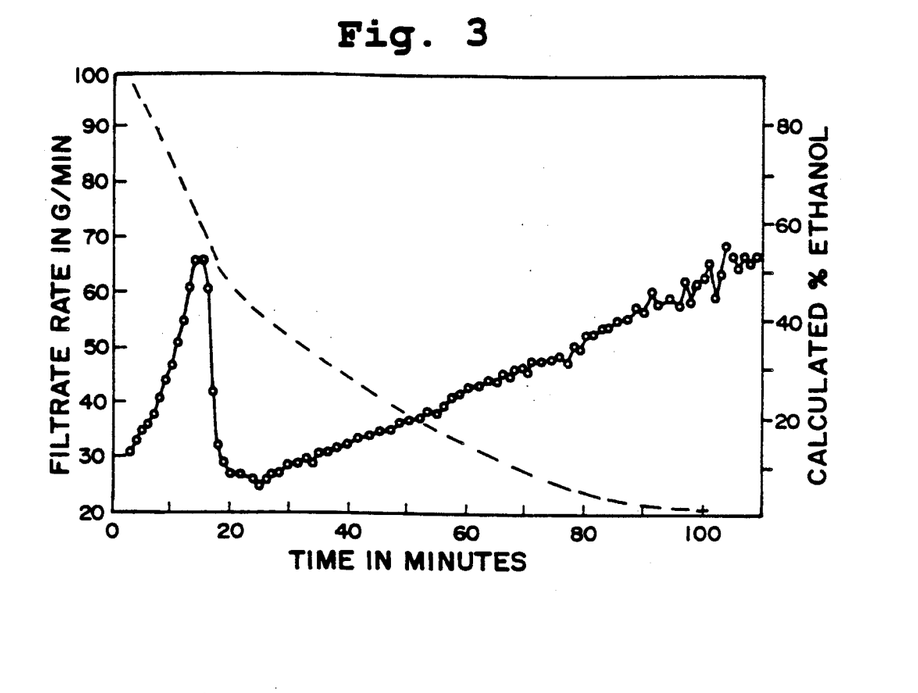
FIG. 3 is a graph of filtration rate (left ordinate) and calculated ethanol concentration (right ordinate), both plotted as a function of filtration time, in a method designed for preparation of liposomes having an average size of about 250 nm.
Figure 4A:
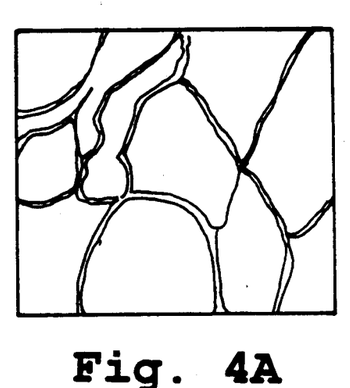
FIGS. 4A-4D are reproductions of photomicrographs of a lipid/solvent/water mixture at increasing water:solvent ratios after initial lipid assembly (4A), at an intermediate stage in liposome formation characterized by heterogeneous size globular lipid structures (4B), during formation of discrete lipid bodies (4C), and after final liposome formation (4D), in a liposome preparation having a mean diameter of about 250 nm.
Figure 4B:
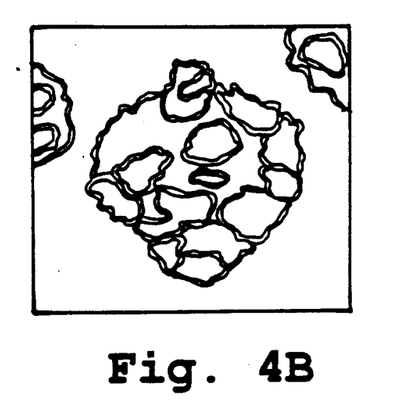
Figure 4C:
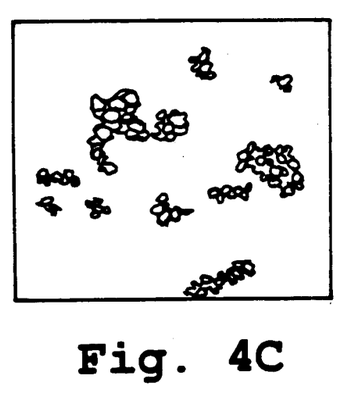
Figure 4D:
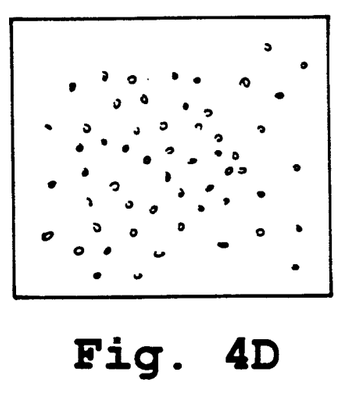

FIG. 3 shows the course of solvent exchange in the liposome-preparation method described in Example 1. Here filtrate weight versus time was measured to determine flow rate during the course of the process. The filtrate rate, expressed in g/min (left ordinate) is shown in open circles in the figure. Samples were collected from the processing tank every minute. Between tubes 6 and 15, the appearance of the mixture changed from clear to translucent, but with no indication of liposome formation. The flow rate curve shows a sharp drop at about 16-17 minutes, indicating initial formation of lipid structures, and tubes 16 and 17 showed large lipid aggregates (FIG. 4A). From sample 16 to sample 19, flow rate was substantially constant, as the large lipid structures showed a gradual reduction in size (FIG. 4B). At tube 24, the lipid structures included a mixture of smaller and medium-size vesicles (4C), and at tube 30, the lipid structures had the appearance of the final uniform-size liposomes seen at the end of the solvent exchange (FIG. 4D).

Figure 5:
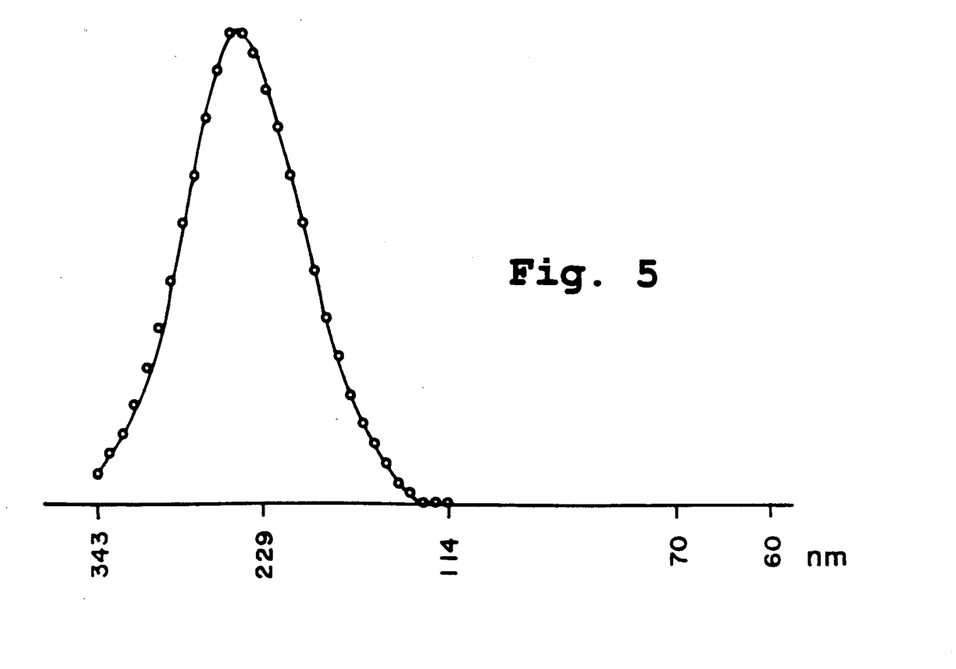
FIG. 5 is a histogram showing the size distribution of liposomes formed in the method described with reference to FIGS. 1-3.

The dotted line in FIG. 3 shows the ethanol concentration at that given time point, calculated on the basis of theoretical dilution in a constant-volume RO system. The first liter of wash volume was supplied by a 158 mM (0.9 M) NaCl solution. At sample 16, when lipid assembly first occurred, about 600 ml of the wash fluid had been added to the tank, producing a salt concentration of about 95 mM, and an ethanol concentration of about 50%. After the entire 1 liter aqueous medium was added (sample 31) an additional 4 liters of distilled water were added, producing a final ethanol concentration of less than 1%. FIG. 5 shows the size distribution of the liposomes formed in the Example 1 method. The size range is from about 110–340 nm and the average size, about 258 nm. As seen, the size distribution of the vesicles is substantially symmetrical about the mean size, in contrast to the size distribution of liposomes prepared by liposome sizing methods which involve shear forces on pre-formed liposomes.

Figure 6:
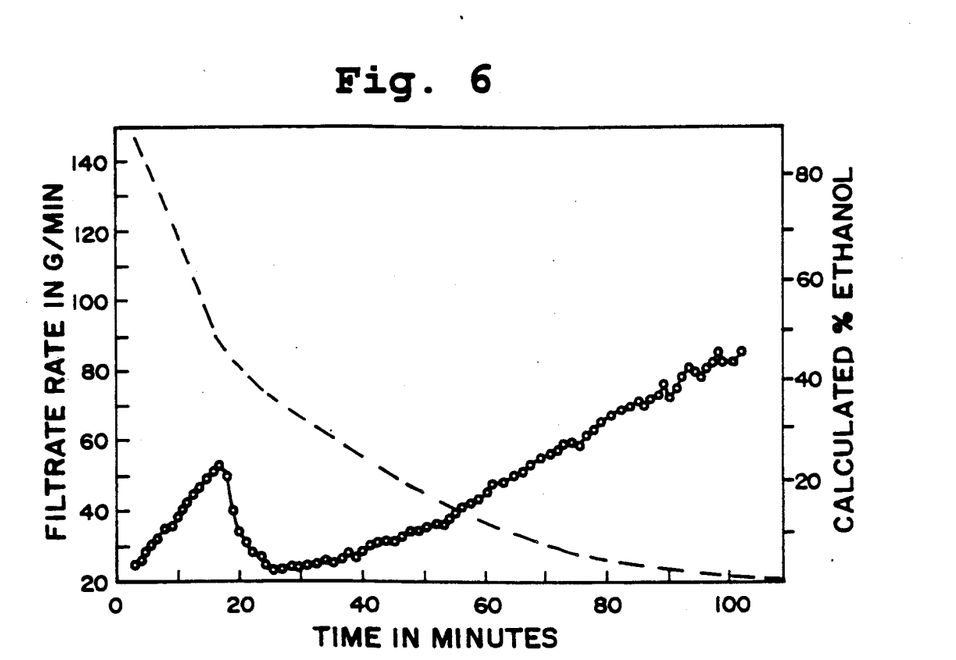
FIG. 6 is a graph of filtration rate (left ordinate) and calculated ethanol concentration (right ordinate), both plotted as a function of reverse-osmosis filtration time, in a method designed for preparation of SUVs.
Figure 7:
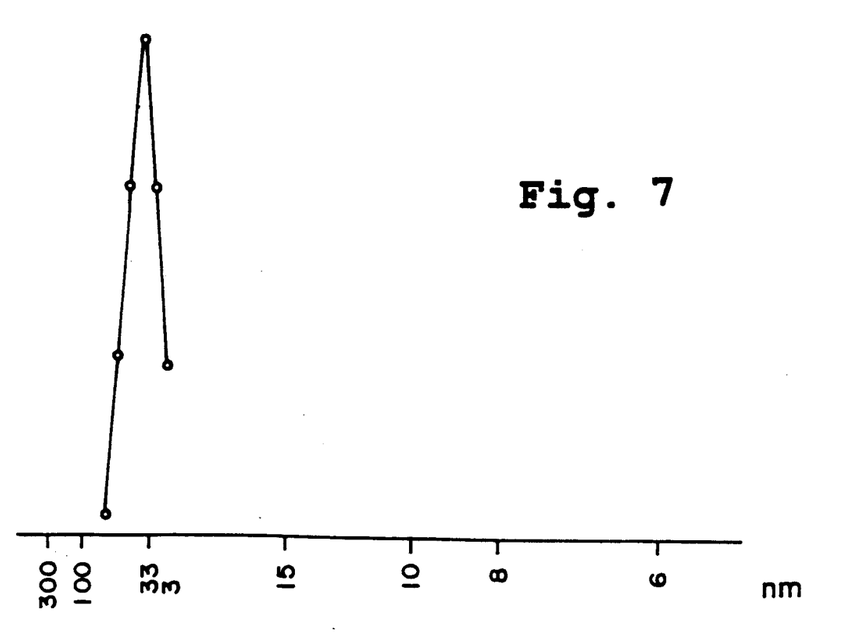
FIG. 7 is a histogram showing the size distribution of liposomes formed in accordance with the method described with reference to FIG. 6.

As indicated above, one aspect of the invention is the ability to control average liposome size, by varying the proportion of charged lipid components and/or ionic strength. The effect of ionic strength can be seen from the RO method described in Example 2. This example is identical to the one in Example 1, except that the ionic strength of the first aqueous medium is only one-tenth as great, i.e., about 15 mM. FIG. 6 shows the change in flow rate (left ordinate) and calculated ethanol concentration (right ordinate). Flow rate was measured by change in filtrate weight over time. The curves are similar to those shown in FIG. 3. The histogram of liposome sizes, seen in FIG. 7, shows a narrow substantially symmetrical distribution of sizes between about 30–50 nm, with a mean diameter of about 33 nm.

The lipid mixtures in Examples 1 and 2 both contained 95% egg PC and 5% egg PG, with buffers at varying ionic strengths. The RO method has also been applied to uncharged lipid compositions, e.g., 100% egg PC. The liposomes formed were uniformly sized SUVs, with a mean diameter of 30–50 nm. Little effect of ionic strength was observed with uncharged lipids.

C. Filter Sterilization and Free-Drug Removal

Lipid structures prepared as above may be readily sterilized by passage through a sterilizing membrane having a particle discrimination size of about 200 nm, such as conventional 220 nm depth or membrane filter.

Where the lipid structures, e.g., liposomes, are formulated to contain an entrapped drug, for use in parenteral drug administration, it is usually desirable to further process the structures to remove free drug, i.e., drug present in the bulk aqueous phase of the suspension. Several methods are available for removing free drug from a liposome suspension. The sized liposome suspension can be concentrated by ultrafiltration, then resuspending the concentrated liposomes in a drug-free replacement medium. Alternatively, gel filtration can be used to separate larger liposome particles from solute (free drug) molecules. Ion-exchange chromatography may provide an efficient method of free drug removal, in instances where a suitable drug-binding resin can be identified. One preferred method of free drug removal is by diafiltration, using a conventional hollow fiber or stacked filter device, which preferably has a molecular weight cutoff of between about 10,000–100,000 daltons.

II. Utility

Liposome suspensions prepared according to the invention are useful in therapeutic applications requiring liposomes with encapsulated or entrapped drug compounds. Uniform-size liposomes having selected sizes less than about 300 nm are useful in particular for parenteral drug administration. As noted above, liposomes in this size range are readily sterilized, give favorable biodistribution, and show less tendency to aggregate on storage.

SUVs formed in accordance with the invention are useful in therapeutic applications which involve tumor targeting or infiltration into hepatic cell liver sites. An advantage of SUVs in ophthalmic liposome applications is greater optical clarity. SUVs are also used for producing larger, high-encapsulation liposomes by freeze-thaw methods.

Other lipid structures prepared according to the method of the invention are also useful in therapeutic or cosmetic formulations. For example, lipid emulsions can be employed for parenteral nutrition, and in concentrated form, can be used in cosmetic cream or paste formulation. Drug lipid complexes particularly involving amphipathic drugs which by themselves are poorly soluble in the blood, are also advantageous for parenteral drug delivery.

From the above, it can be appreciated that the present invention offers a number of advantages over prior art methods of preparing lipid structures, particularly liposomes. Where the liposomes are formed under conditions of substantially constant-volume water/solvent exchange by reverse osmosis, the method produces substantially uniform liposomes sizes, without the requirement for extrusion or other additional liposome sizing steps. This feature is due, at least in part, to the relatively uniform environment of the lipid during liposome formation, i.e., as the lipid structures are gradually converted to small lipid vesicles. In particular, the constant volume ensures that localized lipid dilution effects are avoided. This in contrast with earlier-proposed methods in which the water:solvent ratio in a lipid/solvent/water mixture is raised by dilution with water, e.g., as disclosed in EP patent application No. 0,158,441 for "Liposome-Forming Composition", where formation of relatively heterogeneous-size liposomes is observed.

The present method also provides for immediate solvent removal, thus lessening encapsulation loss. In addition, liposomes formed by the present method have a significantly more symmetrical size distribution about the mean diameter particle size than has been observed in liposomes produced by prior art shear methods.

Inherent in the reverse osmosis system is a uniform environment solute concentration during liposome formation, since localized solute dilution effects are minimized. Solute retention also minimizes problems associated with solvent recovery and loss of non-encapsulated water-soluble drugs. Since the solute compound is neither lost nor diluted during liposome formation, higher encapsulation efficiencies/added compound are possible.

The ability to selectively vary the mean diameter of liposomes, according to lipid composition and/or ionic strength, is another useful feature of the invention. One selected size range, between about 100–300 nm, is advantageous for a variety of parenteral uses, as discussed.

Finally, the invention provides a unique method for forming SUVs, having selected sizes between about 30–80 nm, without shearing-energy input, such as by prolonged sonication or homogenization. Problems of sample contamination, scale-up, oxidative degradation, and extended processing time associated with sonication and homogenization are avoided or minimized.

The following examples illustrate both use and results achievable with the method of the invention, but are in no way intended to limit the scope of the invention.

Materials

Egg phosphatidylcholine (egg PC) was obtained from Lipid KG (Federal Republic of Germany), and egg phosphatidylglycerol (egg PG) was obtained from Avanti Lipids (Birmingham, Ala.). Reverse osmosis membranes, #SK2P473E5, were obtained from Millipore Corp (Bedford, Mass.). A Prolab reverse osmosis (RO) filtration apparatus was obtained from Millipore, Model #MSDPROLAB.

EXAMPLE 1

Preparation of 250 nm Liposomes

Egg PC (38 g) and egg PG (2 g) were dissolved in 473 ml 100% ethanol in a 1 liter flask. After addition of 100 ml distilled water, with stirring, the lipid/ethanol/water mixture was brought to 1 liter with ethanol. The resulting mixture was approximately 50 umole/ml lipid in 90% ethanol.

The mixture was placed in the processing tank of a Prolab filtration apparatus for RO filtration. The RO filter was flushed with a 90% ethanol solution prior to use. The system was run at 80% crossflow with 500 psi back pressure.

NaCl (9 g) was dissolved in 1 liter of distilled water, and this solution was used as the first wash volume, for replacement of ethanol and water lost by RO filtration. Subsequent washes were with 4 liters of distilled water. Samples from the process vessel were collected every minute. Volume replacement with the five aqueous-media volumes was complete after about 110 minutes, and the filtration rate varied from about 30 to 60 ml/min during the five-volume replacement. The final concentration of ethanol in the filtered mixture was less than 1%.

The filtrate weight was measured vs. time to determine flow rate during the filtration period. FIG. 4 (left ordinate) is a plot of flow rate vs time (solid circles). The percentage of ethanol in the filtrate shown in dotted lines in the graph was calculated from theoretical value. At an ethanol concentration corresponding to about 50% ethanol, a sharp decrease in flow rate occurred. This flow gradually increases as the ethanol in the mixture is replaced by water.

To examine the relationship between the formation of lipid structures in the mixture, and the sudden reduction in flow rate observed, samples taken from the processing tank every minute were consecutively numbered by their collection time. Those spanning this portion of the curve were examined by light microscopy. The samples examined were identified as 6, 12, 15, 16, 17, 18, 19, 20, 24, 30, and 36, where sample 16 corresponds to the peak in filtrate rate. The appearance of samples 16 (FIG. 4A), 19 (FIG. 4B), 24 (FIG. 4C), and 30 (FIG. 4D) are discussed above. No change in liposome appearance was observed after sample 30.

The size distribution of the final liposomes was examined with a dynamic light scattering instrument with Nicomp and Brookhaven correlators. FIG. 5 shows a histogram of liposome sizes. The particles have a mean diameter of 258.5 nm, with a standard deviation of 88.9 and a chi square value of 7.1. No evidence of size change in the liposomes was observed during storage.

EXAMPLE 2

Preparation of 33 nm Liposomes

A lipid/solvent/water mixture containing 95% egg PC, 5% egg PG in 90% ethanol was prepared as in Example 1. The ethanol in the mixture was replaced by RO filtration, as above, except that the initial 1 liter wash volume was 0.09% NaCl, rather than 0.9% as used in Example 1. The initial 1 liter aqueous-medium volume was followed by 4 liters of distilled water. One minute samples of the process solution were taken.

FIG. 6 (right ordinate) is a plot of flow rate vs time (solid circles) in the RO procedure, where the calculated percent ethanol is also shown here in dashed line. As above, the RO flow rate peaks at about tube 16 or 17, corresponding to about 50% ethanol, declines sharply, then slowly increases as progressively more of the ethanol in the mixture is replaced.

The size distribution of the final liposomes was examined as above, and FIG. 7 shows a histogram of liposome sizes. The particles have a mean diameter of 33 nm, with a standard deviation of 7.1 nm and a chi square value of 6.8.

Although the invention has been described with respect to particular embodiments and uses, it will be appreciated that the scope of the invention includes a variety of modifications and applications not specifically mentioned.

What is claimed is:

1. A method of forming a suspension of liposomes having uniform sizes in the size range less than about 300 nm, comprising
    forming a mixture of vesicle-forming lipids in a single-phase solvent system comprising a water-miscible lipid solvent, and water, at a water/solvent ratio at which vesicular and amorphous lipid structures, visible by light microscopy, are formed,
    removing solvent and water from the mixture by reverse osmosis, and
    as solvent and water are removed, adding aqueous medium to the mixture, until the mixture reaches a water:solvent ration at which liposome formation occurs.

2. The method of claim 1, wherein the solvent in selected from the group consisting of methanol, ethanol, propanol, isopropanol, and dimethylsulfoxide.

3. The method of claim 2, wherein the solvent is ethanol.

4. The method of claim 1, wherein said adding of aqueous medium is controlled to balance the loss of solvent and water by said removing, to maintain the volume of the mixture substantially constant.

5. The method of claim 4, for producing substantially uniform-size liposomes having a selected mean diameter in the size range less than about 300 nm, wherein the lipids in the mixture are vesicle-forming lipids.

6. The method of claim 5, for producing small, unilamellar vesicles, wherein the vesicle-forming lipids include between 5-10 mole percent negatively charged phospholipid, and the ionic strength of said mixture is between about 5-20 mM.

7. The method of claim 5, for producing small unilamellar vesicles, wherein the vesicle-forming lipids are neutral phospholipids.

8. The method of claim 5, for producing liposomes having a selected mean diameter in the size range between about 200-300 nm, wherein the vesicle-forming lipids include between 5-10 mole percent negatively charged phospholipid, and the ionic strength of said mixture is between about 50-150 mM.

9. A method of forming a suspension of small unilamellar vesicles, comprising
    forming a mixture of vesicle-forming lipids in a single-phase solvent system comprising a water-miscible lipid solvent, said solvent having the ability to pass through a reverse osmotic filter, and water, at a water/solvent ratio at which vesicular and amorphous lipid structures visible by light microscopy are formed, removing solvent and water from the mixture by reverse osmosis, and as solvent and water are removed, adding aqueous medium to the mixutre, at a rate which maintains the volume of the mixture constant, until such small unilamellar vesicles are formed.

10. The method of claim 9, wherein the vesicle-forming lipids include between 5-10 mole percent negatively charged phospholipid, and the ionic strength of said mixture is between about 5-20 mM.

11. The method of claim 9, wherein the vesicle-forming lipids are neutral phospholipids.

* * * * *

UNITED STATES PATENT AND TRADEMARK OFFICE
CERTIFICATE OF CORRECTION

PATENT NO.  : 4,994,213
DATED       : February 19, 1991
INVENTOR(S) : David F. Aitcheson and Renee A. Tenzel It is certified that error appears in the above-identified patent and that said Letters Patent is hereby corrected as shown below:

In Claim 9, column 10, line 64 of the Patent, delete "said solvent having the ability to pass through a reverse osomtic filter".

Signed and Sealed this

Twenty-eighth Day of July, 1992

Attest:

DOUGLAS B. COMER

Attesting Officer

Acting Commissioner of Patents and Trademarks